United States Patent [19]

Regnat et al.

[11] Patent Number: 5,972,825
[45] Date of Patent: Oct. 26, 1999

[54] SUBSTITUTED DIPHENYLDIPHOSPHINES AND A PROCESS FOR THEIR PREPARATION

[75] Inventors: Dieter Regnat, Eppstein; Hans-Jerg Kleiner, Kronberg; Helmut Bahrmann, Hamminkeln, all of Germany

[73] Assignee: Celanese GmbH, Germany

[21] Appl. No.: 09/095,195

[22] Filed: Jun. 10, 1998

Related U.S. Application Data

[62] Division of application No. 08/814,297, Mar. 10, 1997, Pat. No. 5,801,287.

[30] Foreign Application Priority Data

Mar. 11, 1996 [DE] Germany .......................... 196 09 336

[51] Int. Cl.$^6$ .................................. B01J 21/18; C07C 9/50
[52] U.S. Cl. ........................... 502/164; 502/167; 568/17
[58] Field of Search ............................... 568/17; 502/164, 502/167, 162

[56] References Cited

U.S. PATENT DOCUMENTS

| | | | |
|---|---|---|---|
| 4,125,540 | 11/1978 | Sugio et al. | 260/340 |
| 4,556,470 | 12/1985 | Samejima et al. | 204/266 |
| 5,347,045 | 9/1994 | Hermann et al. | 562/35 |
| 5,354,894 | 10/1994 | Devon | 568/17 |
| 5,481,045 | 1/1996 | Hermann et al. | 568/454 |
| 5,565,398 | 10/1996 | Hermann et al. | 502/166 |
| 5,600,006 | 2/1997 | Regnat et al. | 568/16 |

FOREIGN PATENT DOCUMENTS

| | | |
|---|---|---|
| 104 375 | 8/1983 | European Pat. Off. |
| 571 819 | 5/1993 | European Pat. Off. |
| 653 432 | 11/1994 | European Pat. Off. |
| 749973 | 12/1996 | European Pat. Off. |

OTHER PUBLICATIONS

Imre Toth, et al., "Immobilization of rhodium complexes in aqueous HBF$_4$–The enantioselective hydrogenation of prochiral olefins with $\{[CH_3CH_p(p-C_6H_4NMe_2H)_2CH_2 CHP-(p-C_6H_4NMe_2H)_2CH_3]RhNBD\}^{5+}$", Journal of Organometallic Chemistry, 396 (1990) pp. 363–373.

Berge, et al., "Pharmaceutical Salts", Journal of Pharmaceutical Sciences, vol. 66, No. 1 (1977) pp. 1–16.

Imre Toth, et al., Enantioselective Two–Phase Hydrogenation of α–Amino Acid Precursors With Water Soluble Rhodium Complexes of the Cationic Ligand (S,S)–2,4–bis[bis–(p–N, N, N–Trimethylammoniumphenyl) Phosphino]pentane, $[CH_3CH(P(p-C_6H^4NMe_3)_2CH_2 CH(P(p-C_6H_4NMe_3)_2CH_3]_{4+}$, Catalysis Letters 5: (1990) p. 183–188.

Chem. Abs. 100:122286(b) 1983.
Plastics Manufacture, vol. 100 (1984) p. 47.
Chem. Abs. 107:217764 Abstract of Mirabelli (1987).

J Chem Soc Dalton Trans by Chatt, p. 1131–1136, 1985.

*Primary Examiner*—Gary Geist
*Assistant Examiner*—Jean F Vollano
*Attorney, Agent, or Firm*—Connolly & Hutz

[57] ABSTRACT

The present invention relates to compounds of the formula (I)

$$\left( (R^1_2N) \underset{x}{\phantom{x}} \underset{2-m}{\phantom{x}} \right) \left( \underset{2-n}{\phantom{x}} (NR^1_2)_x \right)$$
$$P - R^2 - P$$
$$\left( (R^1_2 \overset{(+)}{H}N)_y \underset{m}{\phantom{x}} \right) \left( \underset{n}{\phantom{x}} (\overset{(+)}{N}HR^1_2)_y \right)$$

$$y(m+n)R^3 \mathord{-\!\!-} A$$

where $R^1$ is H or an alkyl radical having from 1 to 12 carbon atoms, $R^2$ is a straight-chain alkylene radical having from 1 to 8 carbon atoms, an oxygen-containing alkylene radical having from 2 to 4 carbon atoms, a radical of the formula (II) or (III)

(II)

(III)

or a cycloalkylene radical having from 3 to 10 carbon atoms, $R^3$ is an alkyl radical having from 1 to 25 carbon atoms or an aryl radical having from 6 to 10 carbon atoms, A is a radical —COO$^-$ or —SO$_3^-$ and x=0, y=1, m=1 and n=1, or x=1, y=1, m=(1 or 2) and n=(1 or 2), or, if $R^2$ is a radical of the formula (II) or (III), x=1, y=0, m=(0 or 1) and n=(0 or 1), and also a process for their preparation.

12 Claims, No Drawings

SUBSTITUTED DIPHENYLDIPHOSPHINES AND A PROCESS FOR THEIR PREPARATION

This is a division of Ser. No. 08/814,297 filed Mar. 10, 1997 which is now U.S. Pat. No. 5,801,287.

The present invention relates to new compounds of the group consisting of substituted diphenyldiphosphines.

Phosphines have found a wide variety of industrial uses. They are suitable, for example, as antioxidants, metal extractants, flame-retarding impregnants, stabilizers for olefins (US-6-400,168 NTIS); Chem. Abstr. 100; 122286b) and trioxane (U.S. Pat. No. 4,125,540), starting materials for Wittig reagents or ligands for metal complex catalysts. Owing to their wide variety of forms, they are also important precursors for preparing further organic compounds which may or may not contain phosphorus.

Within the group of phosphines, diphosphines play a special role because of their material properties. Since the molecule contains two trivalent phosphorus atoms, they are able to complex numerous metals and metal ions, particularly those from the group consisting of transition metals. The ability to form complexes is attributable to the formation of comparatively stable chelates and can be utilized for preparing corresponding metal complex catalysts which are used in industrial processes.

Within the group of diphosphines, sulfonated diphosphines are of interest because of their particular properties. The sulfonated diphosphines likewise have two trivalent phosphorus atoms and in addition are soluble in water. Such sulfonated diphosphines are described in EP 0 571 819 A. These are sulfonated 2,2'-bis(diphenylphosphinomethyl)-1,1'-binaphthalenes of the formula (A)

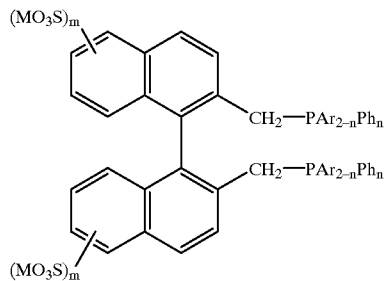

(A)

where Ar is m-$C_6H_4SO_3M$, M is hydrogen, ammonium, a monovalent metal or the equivalent of a polyvalent metal, Ph is a phenyl radical, m is 1 or 2 and n is 0, 1 or 2. These sulfonated diphosphines are used in combination with rhodium as hydroformylation catalysts. Owing to their water solubility, which is attributable to the incorporation of the sulfonic acid or sulfonate groups these diphosphines open up the possibility of carrying out the hydroformylation in a heterogeneous phase. This process variant is particularly advantageous because it opens up a way of separating the catalyst dissolved in water from the water-insoluble reaction product in a simple and gentle manner.

A diphosphine which has become important for the preparation of chiral complexes is S,S-2,4-bis[bis(p-N,N-dimethylaminophenyl)phosphino]pentane (B). As described by Tóth, Hanson and Davis in Catalysis Letters 5 (1990), 183 to 188, this diphosphine can be obtained by reacting R,R-2,4-pentanediol ditosylate with a phosphide KP(p-$C_6H_4$—N($CH_3$)$_2$)$_2$ in accordance with the following reaction scheme:

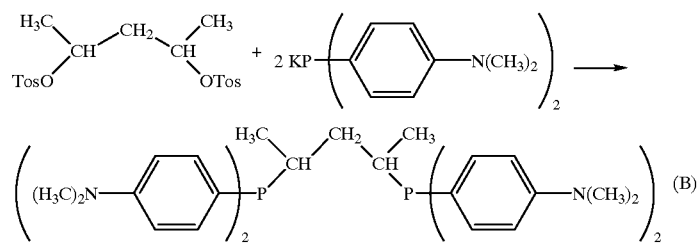

Reaction of the diphosphine (B) with a rhodium complex of the formula (Rh($L_2$)Cl)$_2$, where $L_2$=COD (cyclooctadiene) or NBD (norbornadiene) gives cationic complexes of the type [(diphosphine (B)) Rh$L_2$]$^+$, which can be converted into water-soluble complexes by protonation of the dimethylamino groups present in the diphosphine (B) by means of aqueous HBF$_4$(Tóth, Hanson and Davis, J. Organomet. Chem., 396 (1990) 363 to 373), where, as indicated in the Abstract on page 363, the rhodium complex {[CH$_3$] CHP(p-$C_6H_4N^+(CH_3)_2$H)$_2$CH$_2$CHP(p-$C_6H_4N^+(CH_3)$ $_2$CH$_3$]-RhNBD}$^{5+}$is used for the enantioselective hydrogenation of cinnamic acid derivatives. The structure of the presumed catalytically active intermediate is shown on page 376. The Rh complex contains the diphosphine (B) protonated on all four dimethylamino groups as chelating ligand which is bound to the rhodium via the two phosphorus atoms.

The two previously described catalysts are ones which are soluble in water. The catalysts of the first group comprise the water-soluble sulfonated diphosphines of the formula (A) and those of the second group are soluble in water because of the protonated (by means of aqueous HBF$_4$) dimethylamino groups of the diphosphine (B) bound to rhodium in the form of a chelate.

In view of the particular importance generally attached to the compounds of the group consisting of diphosphines, it is a worthwhile object to provide new compounds from this group in order not only to supplement the range of their possible applications but also to enrich and expand it by means of subtle changes in material properties and variation of structural features. It can be assumed that the chemical characteristics and the structure of the diphosphines exercises an influence on processes in which these diphosphines are used as a catalyst constituent. In particular, an interesting challenge is to combine the particular properties of symmetrically substituted diphosphines with the advantageous influences produced by unsymmetrical substitution and the associated steric and/or electronic effects or any chirality which may additionally result, in order to obtain new unsymmetrical diphosphines which encompass a range of applications which is even larger or different from that of the symmetrically substituted diphosphines.

This object is achieved by compounds of the formula (I)

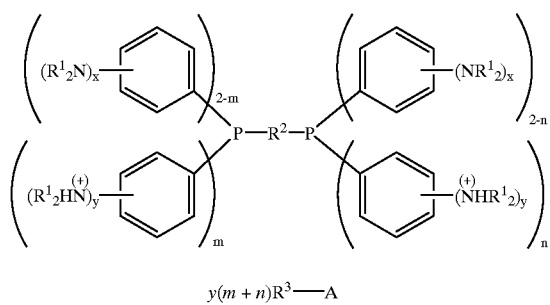

$y(m + n)R^3$——A where $R^1$ is H or an alkyl radical having from 1 to 12 carbon atoms, $R^2$ is a straight-chain alkylene radical having from 1 to 8 carbon atoms, an oxygen-containing alkylene radical having from 2 to 4 carbon atoms, a radical of the formula (II) or (III)

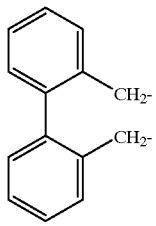

(II)

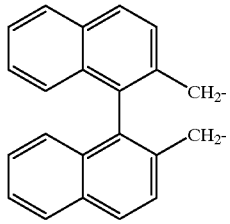

(III)

or a cycloalkylene radical having from 3 to 10 carbon atoms, $R^3$ is an alkyl radical having from 1 to 25 carbon atoms or an aryl radical having from 6 to 10 carbon atoms, A is a radical —COO$^-$ or —SO$_3^-$ and x=0, y=1, m=1 and n=1, or x=1, y=1, m=(1 or 2) and n=(1 or 2), or, if $R^2$ is a radical of the formula (II) or (III), x=1, y=0m=(0 or 1) and n=(0 or 1).

The compounds of the formula (I) containing-N$^+$HR$_2^1$ groups are salts which are=0, m=(0 or 1) and n=(0 or 1).

The compounds of the formula (I) containing-N$^+$HR$_2^1$ groups are salts which are generally insoluble or only slightly soluble in water. On the other hand, despite their salt character, they have a good to very good solubility in organic solvents and are therefore suitable for use in an organic phase.

The compounds of the formula (I) open up a group of substances which can be comparatively simply varied in a wide variety of ways. Firstly the radical $R^1$, secondly the radical $R^2$ and thirdly, if desired, the radical $R^3$ can be altered in order to produce the desired effect on the properties of the resulting compounds, in particular in respect of their solubility in organic solvents or organic media.

The compounds of the formula (I) can also be used as chelating ligands. They are also suitable for preparing further compounds which may or may not contain phosphorus.

In particular, they can be used as a constituent of complex catalysts for the hydroformylation of olefins. This is subject matter of a German Patent Application (Application number 19609337.6) filed on the same day as the present Patent Application.

Of interest are the compounds of the formula (I) in which x=0, y=1, m=1 and n=1 or x=1, y=1, m=(1 or 2) and n=(1 or 2). Of particular interest are the compounds of the formula (I) in which x=1, y=1, m=(1 or 2) and n=(1 or 2), in particular those in which m=2 and n=2. For the sake of completeness, it may be mentioned that x and y can each be, independently of one another, 0 or 1 and m and n can generally be, independently of one another, 0, 1 or 2, and x and y on the one hand and m and n on the other hand are independent of one another.

The $R_2^1$N- and the $R_2^1$HN$^+$-groups can be located in any position on the benzene ring, in particular in the meta position or para position, preferably in the para. Of particular interest are the compounds of the formula (I) in which $R^1$ is a methyl radical, since they are particularly readily obtainable.

The radical $R^2$ connecting the two P atoms is, as already mentioned in the introduction, a straight-chain alkylene radical having from 1 to 8 carbon atoms, an oxygen-containing alkylene radical having from 2 to 4 carbon atoms, a radical of the formula (II) or (III)

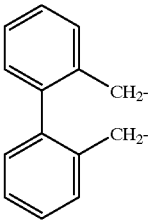

(II)

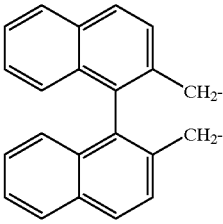

(III)

or a cycloalkylene radical having from 3 to 10 carbon atoms, in particular an alkylene radical having from 1 to 4 carbon atoms or a radical —(CH$_2$)$_2$—O—(CH$_2$)$_2$—, preferably a trimethylene or tetramethylene radical.

However, the radicals of the formulae (II) and (III) are also of importance since they can give the diphosphines chiral properties. This is the case when the two benzene or naphthyl rings do not lie in one and the same plane, but are twisted about the bond linking the two rings and free rotation about this bond is no longer possible because of steric hindrance. This is sometimes the case for comparatively large radicals present on the CH$_2$ group. The radicals located on $R^2$ in the formula (I) and enclosing the P atom are sufficiently bulky to allow, in particular, the radical (III) to become chiral in this way.

This gives diphosphines of the formula (I) which are additionally chiral. Chiral diphosphines generally open up a different sort of application area from symmetrically substituted, nonchiral diphosphines, which field usually goes beyond that of nonchiral diphosphines.

As mentioned above, the radical $R^3$ is an alkyl radical having from 1 to 25 carbon atoms or an aryl radical having from 6 to 10 carbon atoms, in particular an alkyl radical having from 12 to 24 carbon atoms or an aryl radical having from 6 to 7 carbon atoms, preferably an alkyl radical having from 14 to 22 carbon atoms.

A is, as already mentioned in the introduction, a radical —COO$^-$ or —SO$_3^-$, in particular a radical —COO$^-$.

Without claiming to be exhaustive, some suitable representatives of the compounds of the formula (I) may be mentioned at this point:

1,4-bis(4-dimethylaminophenyl-4-dimethylammoniumphenyl-phosphino)butane distearate, 1,3-bis(4-dimethylaminophenyl-dimethylammoniumphenyl-phosphino)propane distearate, 1,4-bis(4-dimethylaminophenyl-4-dimethylammoniumphenyl-phosphino)butane dipalmitate, 1,3-bis[bis(dimethylammoniumphenyl)phosphino]propane tetrapalmitate, 2,2'-bis[bis(dimethylammoniumphenyl)phosphinomethyl] biphenyl tetrapalmitate.

The present invention also provides a process for preparing the compounds of the formula (I). It comprises reacting a phosphine oxide of the formula (IV) and (V)

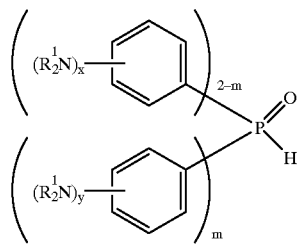

(IV)

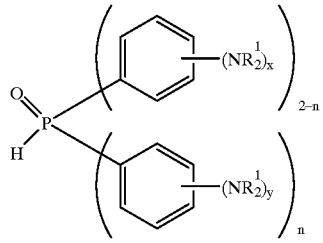

(V)

where $R^1$, x, y, m and n are as defined above, with a dihalide X—$R^2$—X, where X is Cl or Br and $R^2$ is as defined above, with a base in the presence or absence of a solvent at from −20 to 100° C. to give a diphosphine oxide of the formula (VI)

(VI)

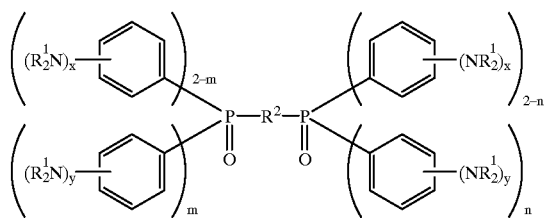

reducing the diphosphine oxide of the formula (VI) in the presence or absence of a solvent with a silane of the formula HSiCl$_a$R$_b$, where a=(2 or 3), b=(0 or 1) and (a+b)=3 and R is a methyl radical or a phenyl radical, at from 80 to 160° C. to give a diphosphine of the formula (VII)

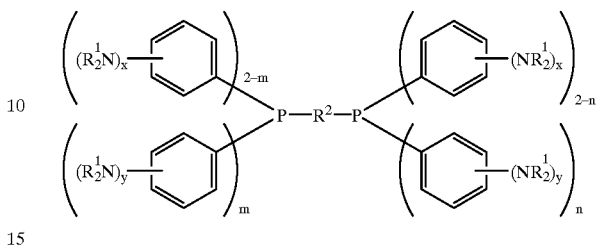

(VII)

and, if desired, reacting the diphosphine of the formula (VII) with an acid of the formula $R^3$—A—H, where $R^3$ and A are as defined above.

The meanings of $R^1$, x, y, m, n, $R^2$, $R^3$ and A can in each case be taken from those given in connection with the description of the compounds of the formula (I). For this reason, the meanings of $R^1$, x, y, m, n, $R^2$, $R^3$ and A will not be listed again at this point.

The process of the invention has been found to be very versatile and can be utilized flexibly. This is because it allows, advantageously, the radical $R^1$ to be selected freely, i.e. without the radicals $R^2$ and $R^3$ having to be taken into account. The same applies to the radical $R^2$. This radical too can be selected independently of the radicals $R^1$ and $R^3$. Finally, the radical $R^3$ too can be inserted in the compound of the formula (I) without restrictions being imposed by the prior selection of $R^1$ and $R^2$. This flexibility of the process of the invention is based on the fact that, on the one hand, it is possible to freely select the phosphine oxides of the formula (IV) and (V) containing the radicals $R^1$ and, on the other hand, it is possible to freely select the dihalide of the formula X—$R^2$—X and in addition, independently of these building blocks, any desired compound $R^3$—A—H can be used in the preparation. This gives the process a high degree of utility and additionally ensures that a very wide range of compounds of the formula (I) are obtainable.

The phosphine oxide of the formula (IV) and the dihalide X—R—X are usually reacted in a molar ratio of 1:(1 to 5) and the reaction product, if desired after separating off excess dihalide, is subsequently reacted with the phosphine oxide of the formula (V). This gives diphosphine oxides of the formula (VI) containing two different phosphine oxide groups.

In many cases it is sufficient to react the dihalide X—$R^2$—X with the phosphine oxide of the formula (IV) or with the phosphine oxide of the formula (V) in a molar ratio of 1:(2 to 2.2). This gives diphosphine oxides containing two identical phosphine oxide groups.

The reaction of the phosphine oxides of the formulae (IV) and (V) with the dihalide is carried out with addition of a base in order to bind hydrogen halide, namely HCl or HBr, liberated in this reaction. The base used can be a compound MeH, where Me is Li, Na or K, or a compound LiR', where R' is an alkyl radical having from 1 to 4 carbon atoms or a phenyl radical. It is also possible to use mixtures of the abovementioned bases. As mentioned above, the diphosphine oxide of the formula (VI) is reacted in the presence or absence of a solvent with a silane of the formula HSiCl$_a$R$_b$, where a and b are as defined above, in particular with a silane of the formula HSiCl$_2$R, where R is a methyl radical or phenyl radical, at a temperature from 100 to 150° C. Although this reduction can also be carried out at higher and lower temperatures, the temperature range from 100 to 150° C. has been found to be advantageous and sufficient for many cases.

The reduction of the diphosphine oxide of the formula (VI) is preferably carried out in the presence of a solvent. An organic solvent which is inert under the reduction conditions is usually used for this purpose. Without claiming to be exhaustive, mention may be made of acetonitrile, toluene or xylene as solvent.

The reduction of the diphosphine oxide of the formula (VI) gives a diphosphine of the formula (VII) which can be used directly in unchanged form as chelating ligand. However, it is usually used as starting material for the —N$^+$HR$_2^1$-containing compounds of the formula (I). For this purpose, the diphosphine of the formula (VII) is reacted with a compound of the formula R$^3$—A—H, where R$^3$ is an alkyl radical having from 1 to 25, in particular from 12 to 24, preferably from 14 to 22, carbon atoms or an aryl radical having from 6 to 10, in particular 6 or 7, carbon atoms and A is a —COO$^-$ or —SO$_3^-$, in particular —COO$^-$, group, thus protonating one or more or all of the —NR$_2^1$ groups present in the diphosphine of the formula (VII).

The diphosphine of the formula (VII) and the compound R$^3$—A—H, i.e. the protonating acid, are used in a ratio such that from 1 to 2 mol, in particular from 1 to 1.5 mol, preferably from 1 to 1.1 mol, of the compound R$^3$—A—H are employed per equivalent of —NR$_2^1$ groups to be protonated.

While Tóth states in J. Organomet. Chem. 396 (1990), page 367 under the item "conclusions", that a ten-fold excess of HBF$_4$ is required to fully protonate the four dimethylamino groups of the diphosphine (B) coordinated to rhodium in the form of a chelate, it appears surprising that the protonation of the uncoordinated diphosphine (VII) proceeds without significant problems even when using acids weaker than HBF$_4$ and, in addition, protonation of the two phosphorus atoms can be substantially or virtually completely avoided. Protonation of the two phosphorus atoms would lead to the diphosphine losing its ability to form chelates and as a result no longer being suitable as a ligand or constituent of metal complex catalysts.

The process of the invention can be carried out continuously or batchwise. A batchwise procedure is particularly suitable. The process of the invention can be carried out under atmospheric pressure, under reduced pressure or under superatmospheric pressure. It is usually carried out under atmospheric pressure or the reaction pressure established under the respective reaction conditions.

The examples below illustrate the invention without restricting it to them.

Experimental Part

EXAMPLE 1

1a) Preparation of 1,4-bis[bis(4-dimethylaminophenyl) phosphinyl]butane 14.42 g (50 mmol) of bis(4-dimethylaminophenyl) phosphine oxide are initially charged in 100 ml of dry tetrahydrofuran in an argon atmosphere while stirring and 32 ml of a 1.6 molar solution of n-butyllithium in hexane (50 mmol) are added dropwise at 25° C. The mixture is stirred for 2.5 hours at 25° C. and 5.4 g (25 mmol) of 1,4-dibromobutane are then added dropwise. The mixture is subsequently stirred for 2 hours at 25° C. and 30 ml of water are then added dropwise. The solid formed is filtered off and recrystallized from acetonitrile. This gives 12.5 g of colorless crystals, corresponding to a yield of 79%.

$^{31}$P-NMR (CD$_3$OD): δ=39.2 ppm

1b) Preparation of 1,4-bis[bis(4-dimethylaminophenyl) phosphino]butane 6.1 g (10 mmol) of 1,4-bis[bis(4-dimethylaminophenyl) phosphinyl]butane and 9.3 g (50 mmol) of tri-n-butylamine are initially charged in 30 ml of o-xylene in an argon atmosphere. 5.75 g (50 mmol) of methyldichlorosilane are slowly added dropwise with the reaction mixture warming up to 50° C. It is subsequently heated to 100° C. and stirred for 4 hours, then heated to 145° C. and stirred for 16 hours. Cooling the clear solution results in formation of colorless crystals which are filtered off and washed with 10 ml of degassed o-xylene. Drying in a high vacuum gives 5.5 g of colorless crystals, corresponding to a yield of 95%.

$^{31}$P-NMR (CDCl$_3$): δ=−19.9 ppm

1c) Preparation of a Dipalmitate Salt of 1,4-bis[bis(4-dimethylaminophenyl)-phosphino]butane 3.5 g (6.05 mmol) of 1,4-bis[bis(4-dimethylaminophenyl) phosphino]butane are initially charged in 20 ml of dry degassed o-xylene in an argon atmosphere and admixed with 3.1 g (12.5 mmol) of palmitic acid. The mixture is heated at 100° C. for 2 hours and subsequently cooled to 25° C. Filtration, washing with xylene and drying in a high vacuum gives 6.9 g of colorless crystals.

$C_{68}H_{112}N_4O_4B_2$

| calculated: | C 71.5% | H 9.9% | N 4.9% | O 5.6% | P 5.6% |
| --- | --- | --- | --- | --- | --- |
| found: | C 71.4% | H 9.8% | N 5.0% | O 5.7% | P 5.5% |

$^{31}$P-NMR (CDCl$_3$): δ = −19.9 ppm.

EXAMPLE 2

2a) Preparation of 1,3-bis[bis(4-dimethylaminophenyl) phosphinyl]propane 14.42 g (50 mmol) of bis(4-dimethylaminophenyl) phosphine oxide are initially charged in 100 ml of dry tetrahydrofuran in an argon atmosphere and 32 ml of a 1.6 molar solution of n-butyllithium in hexane (50 mmol) are added dropwise at 25° C. The mixture is stirred for 2.5 hours at 25° C. and 5.05 g (25 mmol) of 1,3-dibromopropane are then added dropwise. The mixture is subsequently stirred for 2 hours at 25° C. and 30 ml of water are then added dropwise. The solvent is distilled off under reduced pressure and the residue is extracted with 100 ml of dichloromethane/ 50 ml of water. The organic phase is separated off, dried with magnesium chloride and evaporated under reduced pressure, forming a colorless crystalline material which is recrystallized from acetonitrile. This gives 12.3 g of colorless crystals, corresponding to a yield of 78%.

$^{31}$P-NMR (CDCl$_3$): δ=33.5 ppm.

2b) Preparation of 1,3-bis[bis(4-dimethylaminophenyl) phosphino]propane 12.0 g (19.5 mmol) of 1,3-bis[bis(4-dimethylaminophenyl)phosphinyl]propane and 24 ml (100 mmol) of tri-n-butylamine are initially charged in 80 ml of o-xylene in an argon atmosphere while stirring. 14.4 ml (100 mmol) of phenyldichlorosilane are slowly added dropwise. The mixture is heated to 145° C., stirred for 6 hours and the solvent is distilled off under reduced pressure. Cooling the clear solution results in formation of colorless crystals which are filtered off. The crystals obtained are suspended in 100 ml of degassed o-xylene and extracted with 20 ml of 2N sodium hydroxide solution. The organic phase is separated off, dried with sodium sulphate and evaporated under reduced pressure. This gives 10.8 g of colorless solid, corresponding to a yield of 95%.

$^{31}$P-NMR (CDCl$_3$): δ=−21.2 ppm.

2c) Preparation of a Tetrapalmitate Salt of 1,3-bis[bis(4-dimethylaminophenyl)phosphino]propane 2.9 g (5 mmol) of 1,3-bis[bis(4-dimethylaminophenyl) phosphino]propane are initially charged in 20 ml of dry, degassed o-xylene in an argon atmosphere and admixed with 5.1 g (20 mmol) of palmitic acid. The mixture is heated to 100° C., stirred for 2 hours and subsequently cooled to 25° C. and evaporated to dryness under reduced pressure. This gives 8.0 g of colorless crystals.

$C_{99}H_{174}N_4O_8P_2$ (1612.48)
| | | | | | |
|---|---|---|---|---|---|
| calculated: | C 73.7% | H 10.9% | N 4.0% | O 7.9% | P 3.9%. |
| found: | C 73.7% | H 10.8% | N 4.1% | O 7.9% | P 3.9% |

$^{31}$P-NMR (CDCl$_3$): δ = −21.2 ppm.

EXAMPLE 3

3a) Preparation of 2,2'-bis(phenyl-4-dimethylaminophenyl-phosphinylmethyl)-1,1'-binaphthyl 28.7 g (105 mmol) of ethyl phenyl-4-dimethylaminophenylphosphinite are added dropwise over a period of one hour to a solution of 22.01 g (50 mmol) of 2,2'-bis(bromomethyl)-1,1'-binaphthyl in 120 ml of o-xylene heated to 130° C. The mixture is stirred for 4 hours at 140° C., cooled to 20° C. and the precipitated solid is filtered off. This gives 28.1 g of colorless crystals, corresponding to a yield of 73%.

$^{31}$P-NMR (CDCl$_3$): δ=30.6, 30.5 ppm.

3b) Preparation of 2,2'-bis(phenyl-4-dimethylaminophenyl-phosphinomethyl)-1,1'-binaphthyl 19.87 g (25.8 mmol) of 2,2'-bis(phenyl-4-dimethylaminophenyl-phosphinylmethyl)-1,1'-binaphthyl and 15.5 ml (66 mmol) of tributylamine are initially charged in 80 ml of degassed, dry o-xylene in an argon atmosphere while stirring and 9.4 ml (65 mmol) of phenyldichlorosilane are added dropwise. The mixture is subsequently heated at 145° C. for 7 hours while stirring. The reaction mixture is cooled, admixed with 50 ml of degassed 32% strength sodium hydroxide solution and the phases are separated. The organic phase is concentrated and the solid formed is filtered off and recrystallized from acetonitrile. This gives 14.3 g of colorless crystals, corresponding to a yield of 75%.

$^{31}$P-NMR (CDCl$_3$): δ=−12.6, −14.4 ppm.

3c) Preparation of a Dipalmitate Salt of 2,2'-bis(phenyl-4-dimethylaminophenyl-phosphinomethyl)-1,1'-binaphthyl 4.44 g (6.05 mmol) of 2,2'-bis(phenyl-4-dimethylaminophenyl-phosphinomethyl)-1,1'-binaphthyl are initially charged in 20 ml of dry, degassed o-xylene in an argon atmosphere and admixed while stirring with 3.1 g (12.1 mmol) of palmitic acid. The mixture is subsequently heated at 100° C. for 2 hours and then cooled to 25° C. The solvent is completely distilled off in a high vacuum. This gives 7.54 g of a colorless substance.

$^{31}$P-NMR (CDCl$_3$): δ=−12.6, −14.4 ppm

We claim:

1. A complex catalyst for the hydroformylation of an olefin which comprises a compound of the formula I

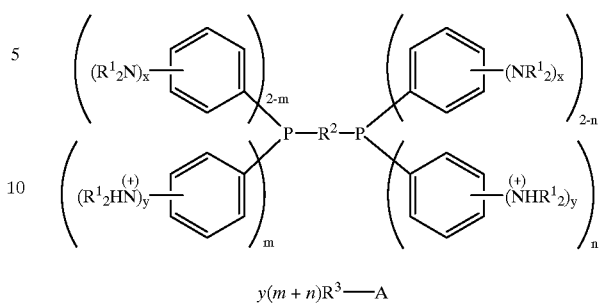

$y(m + n)R^3$——A where $R^1$ is H or an alkyl radical having from 1 to 12 carbon atoms, $R^2$ is a straight-chain alkylene radical having 1 to 8 carbon atoms, an oxygen-containing alkylene radical having from 2 to 4 carbon atoms, a radical of the formula (II) or (III)

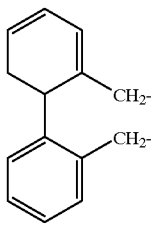

(II)

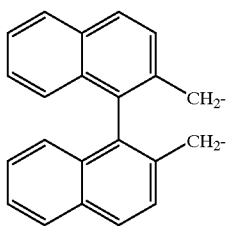

(III)

or a cycloalkylene radical having 3 to 10 carbon atoms, $R^3$ is an alkyl radical having from 1 to 25 carbon atoms or an aryl radical having from 6 to 10 carbon atoms, A is a radical —COO$^-$ and x=0, y=1, m=1 and n=1, or x=1, y=1, m=1 or 2 and n=1 or 2, or if $R^2$ is a radical of the formula (II) or (III), x=1, y=0, m=0 or 1.

2. The catalyst as claimed in claim 1, wherein x=0, y=1, m=1 and n=1 or x=1, y=1, m=1 or 2 and n=1 or 2.

3. The catalyst as claimed in claim 1, wherein x=1, y=1, m=1 or 2 and n=1 or 2.

4. The catalyst as claimed in claim 1, wherein the $R_2^1$N- and $R_2^1$HN$^+$-groups are in the meta or para position to the bond which connects the benzene ring to the respective P atom.

5. The catalyst as claimed in claim 1, wherein the $R_2^1$N- and $R_2^1$HN$^+$-groups are in the para position to the bond which connects the benzene ring to the respective P atom.

6. The catalyst as claimed in claim 1, wherein $R^1$ is an alkyl radical having from 1 to 4 carbon atoms.

7. The catalyst as claimed in claim 1, wherein $R^1$ is a methyl or ethyl radical.

8. The catalyst as claimed in claim 1, wherein $R^1$ is a methyl radical.

9. The catalyst as claimed in claim 1, wherein $R^2$ is an alkylene radical having carbon atoms or a radical —(CH$_2$)$_2$—O—(CH$_2$)$_2$—.

10. The catalyst as claimed in claim 1, wherein $R^2$ is a trimethylene or tetramethylene radical.

11. The catalyst as claimed in claim 1, wherein $R^3$ is an alkyl radical having from 12 to 24 carbon atoms or an aryl radical having 6 or 7 carbon atoms.

12. The catalyst as claimed in claim 1, wherein $R^3$ is an alkyl radical having 14 to 22 carbon atoms.

\* \* \* \* \*